United States Patent [19]

Mayes

[11] Patent Number: 5,697,522
[45] Date of Patent: Dec. 16, 1997

[54] TEST TUBE DROP DISPENSER

[75] Inventor: Ronald A. Mayes, Beaumont, Tex.

[73] Assignee: Helena Laboratories Corporation, Beaumont, Tex.

[21] Appl. No.: 548,452

[22] Filed: Oct. 26, 1995

Related U.S. Application Data

[63] Continuation-in-part of Ser. No. 313,400, Sep. 27, 1994, abandoned, which is a continuation of Ser. No. 60,977, May 14, 1993, abandoned.

[51] Int. Cl.$^6$ .................................................. B67B 7/00
[52] U.S. Cl. ............................ 222/1; 222/82; 222/209; 222/420; 604/411
[58] Field of Search .......................... 222/1, 81, 82, 222/83, 162, 184, 185, 209, 211, 214, 420, 563, 175, 179.5; 604/407, 411, 418; 401/134, 193; 239/271, 273

[56] References Cited

U.S. PATENT DOCUMENTS

| | | | |
|---|---|---|---|
| 3,366,278 | 1/1968 | Fobes | 222/82 |
| 3,788,528 | 1/1974 | Ogle | 222/420 X |
| 4,085,866 | 4/1978 | Fekl | 222/158 |
| 4,411,661 | 10/1983 | Kersten | 604/411 |
| 5,024,355 | 6/1991 | Jouillat et al. | 222/422 X |
| 5,048,723 | 9/1991 | Seymour | 222/88 X |
| 5,086,950 | 2/1992 | Crossdale et al. | 222/185 X |
| 5,114,033 | 5/1992 | Golias et al. | 222/82 |
| 5,139,174 | 8/1992 | Golias | 222/420 X |
| 5,163,583 | 11/1992 | Whitworth | 222/1 |
| 5,180,083 | 1/1993 | Carlson | 222/185.1 |
| 5,263,787 | 11/1993 | Wilcox et al. | 222/179.5 |
| 5,286,453 | 2/1994 | Pope . | |

*Primary Examiner*—Andres Kashnikow
*Assistant Examiner*—Lisa Ann Douglas
*Attorney, Agent, or Firm*—Dorsey & Whitney

[57] ABSTRACT

A method and apparatus is provided for discharging the contents of a sealed container, such as a test tube. The apparatus includes a member to penetrate the closure of a test tube and provides for reduction of the volume within the test tube, thus pressurizing the test tube contents so that fluid is dispensed through a fluid flow path. The apparatus further including a stabilizing system that facilitates the accurate dispensing of fluid onto a target surface. The method includes pressurizing the contents of the test tube by reducing the volume of the test tube, and providing a flow path such that fluid may be dispensed through the flow path in response to the reduction of the test tube volume.

8 Claims, 2 Drawing Sheets

TEST TUBE DROP DISPENSER

This is a continuation-in-part of application Ser. No. 08/313,400, filed Sep. 27, 1994, now abandoned which is a continuation of application Ser. No. 08/060,977, filed May 14, 1993 (now abandoned).

BACKGROUND OF THE INVENTION

The present invention relates generally to a method and an apparatus for dispensing the contents of a sealed fluid container, and has particular utility in discharging the contents of a test tube, serum collection tube, or the like.

Test tubes are frequently used as collection containers for blood specimens and other liquids, such as biological fluids. Typically, when blood is to be collected, an anticoagulant is placed in the test tube and a blood specimen is withdrawn from a patient and placed into the test tube, whereupon the test tube is sealed with a resilient closure such as a rubber stopper or the like.

The task of conveniently and efficiently dispensing the liquid from the test tube is encountered routinely by laboratory workers in a variety of circumstances. The devices and methods disclosed in the prior art to facilitate this task present various shortcomings based on their relative complexity and effectiveness.

For example, U.S. Pat. No. 5,139,174 issued Aug. 18, 1992 to Golias, discloses a fluid dispensing device necessarily requiring the removal of the test tube closure before the dispensing device can be attached to the open end of the tube. There are several problems associated with the removal of the tube closure, such as contamination of the fluid to be tested, fluid spillage, and possible exposure of the laboratory technician to any diseases carried by the fluid.

U.S. Pat. No. 5,114,033 issued May 19, 1992 to Golias et al. circumvents the problem of having to remove the original test tube closure encountered above by providing a holder featuring at least two cannulas, or needles. The needles or cannulas are used to puncture the test tube closure. In certain embodiments illustrated in the '033 patent the two cannulas are mounted within a single body with the body having a barb to puncture the tube closure. In all embodiments, one of the cannulas delivers air into the tube by means of a separate pump, while the other cannula is used to deliver fluid from the test tube. Although the '033 patent obviates the problem of having to remove the original closure of the test tube, it requires the provision of a suitable clearance between the inner diameter of the second cannula and the outer diameter of the delivery tube therein in order to strike a balance between keeping pumping efficiency at a maximum and maintaining responsiveness of the delivery system to the pumping pressure. Furthermore, the '033 patent requires the provision of a separate compressible pump or bulb. Each of the above patents is hereby incorporated by reference.

An additional shortcoming of the prior art is the issue of the stability of the dispenser when dispensing liquids versus the ability to quickly and accurately dispense fluid onto a desired surface, such as a slide. For example, U.S. Pat. No. 5,286,453 issued Feb. 15, 1994 to Pope, discloses a device for dispensing a liquid from a tube having a circumferential support that may assist in stabilizing the dispenser when dispensing liquid therefrom. However, the support does not permit the user to view or sight either the surface onto which liquid is to be dispensed or the liquid dispensed therefrom.

SUMMARY OF THE INVENTION

It is an object of the present invention to provide an improved, simple and effective fluid discharge apparatus which is readily insertable into a test tube closure and adaptable to a range of test tube opening sizes.

A further object of the present invention is to obviate the need for separate pumping means such as bulbs or bellows, or the need for separate fluid delivery tubes which could require the determination of an optimum clearance between the tubes and the bores into which they are to be inserted.

It is another object of the present invention to provide an improved, simple and effective method for discharging fluid from a sealed container such as a test tube.

It is a further object of the present invention to provide an apparatus having a stabilizing means that stabilizes and supports the apparatus yet permits the user to view the target surface and the liquid dispensed from the apparatus.

These objects and others to become apparent as the specification progresses are accomplished by the present invention, according to which, briefly stated, a fluid dispensing assembly for dispensing the fluid contents of a test tube includes means for pressurizing the chamber within the test tube by reducing the volume therein, in response to which the contents of the test tube are discharged. The present invention further contemplates the method of pressurizing the chamber within the test tube by reducing the volume therein, in response to which the contents of the test tube are discharged.

BRIEF DESCRIPTION OF THE DRAWINGS

The foregoing objects of the invention, together with other objects and advantages which may be attained by its use, will become more apparent upon reading the following detailed description of the invention taken in conjunction with the drawings. In the drawings, wherein like reference numerals identify corresponding components.

DESCRIPTION OF THE PREFERRED EMBODIMENT

Figure 1:
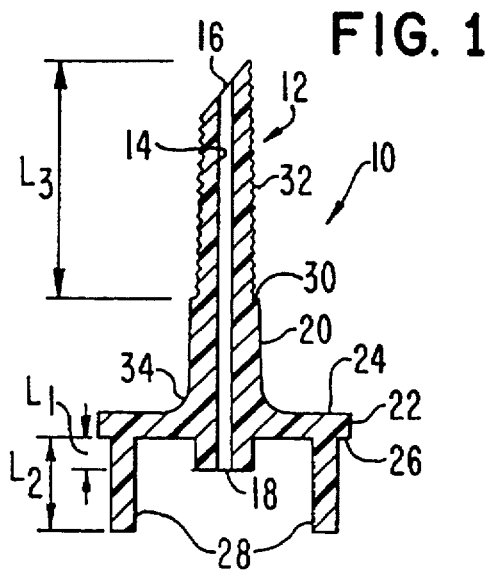
FIG. 1 is a sectional side elevational view of the apparatus of the present invention according to a preferred embodiment of the invention, the apparatus being enlarged for clarity of illustration.
Figure 2:
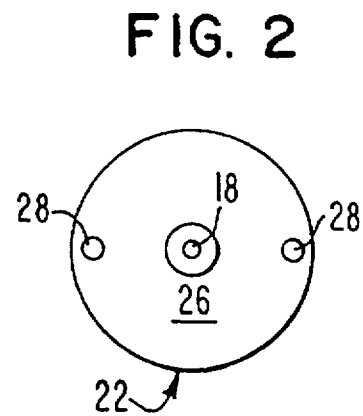
FIG. 2 is a bottom plan view of the apparatus shown in FIG. 1.

Referring now to FIGS. 1 and 2, a fluid dispenser 10 is shown which includes a hollow needle or cannula portion 12 containing a dispensing bore or fluid flow path 14 therein. Bore 14 extends the full length of the cannula portion and connects a fluid inlet at one end of the cannula, such as from a puncturing cannula tip 16 to a fluid outlet 18 at the opposite end of the cannula. Tip 16 may be pointed or chamfered to facilitate insertion through a conventional test tube closure.

Cannula portion 12 includes a stem portion 20 terminating in a base 22, preferably formed integral with the stem 20. The base 22 has two opposed surfaces 24, 26, with surface 24 positioned toward tip 16 and surface 26 positioned away from tip 16. The base is provided with stabilizing means 28, such as projections or legs 33 extending from base surface 26 in a direction away from cannula tip 16. Fluid outlet 18 of bore 14 extends beyond base surface 26 in the direction of stabilizing means 28, and has a length L1 which is preferably shorter than the length L2 of stabilizing means 28 when measured in a direction away from tip 16.

Figure 5:
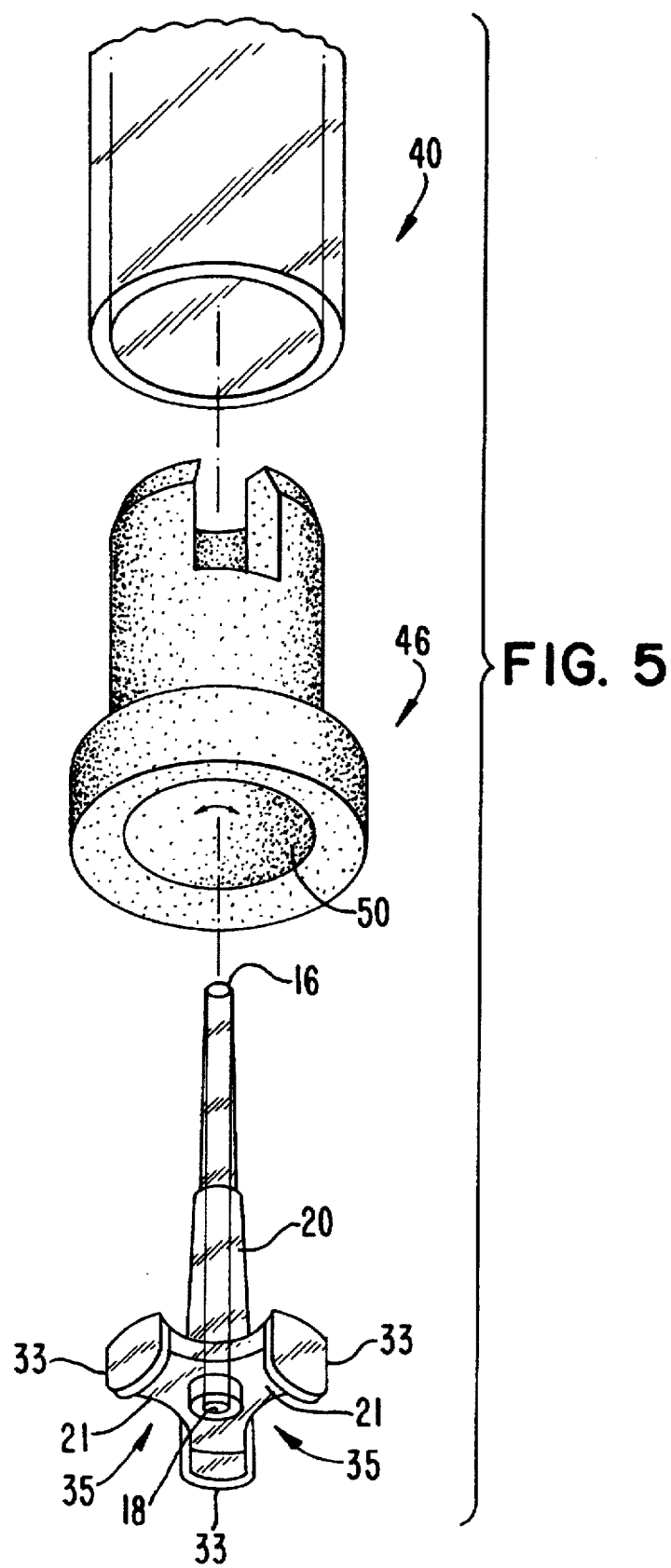
FIG. 5 is an exploded perspective of a test tube, test tube stopper and the apparatus of the present invention.

With reference to FIG. 5 the base 22 may contain at least three flanges 21 having opposed surfaces with one surface positioned toward tip 16 and the other surface positioned away from tip 16. Depending from each flange at a 90° angle from each flange 21 and in a direction away from cannula tip 16 is a leg 33. Each leg 33 and flange 21 element is separated from the other elements by a viewing space 35. The legs 33 and viewing spaces 35 comprise the stabilizing means 28. The legs 33 are all of equal length.

The legs 33 are oriented to provide stability such that the apparatus 10 may be placed upon a target surface and will remain in a vertical orientation, perpendicular to the target surface, without further support. The viewing spaces 35 are oriented to permit a user to view both the target surface and the liquid to be dispensed from the dispenser 10. The stabilizing means 28 facilitates the quick and accurate dispensing of the fluid onto the target surface because the surface may be maneuvered between the legs 33 and the surface sighted through the viewing spaces 35. Further, because the legs 33 are of equal length, they ensure, when contacted with a supporting surface, (which may be the target surface itself, such as a slide, or a surface that supports the target surface, such as a bench top) that the outlet 18 is properly oriented perpendicular to the target surface to permit the accurate delivery of fluid onto the surface.

In a further embodiment, the legs 33 are transparent, thereby permitting the user to view directly through the stabilizing means 28.

Cannula 12 is provided with a stop means 30 intermediate base surface 24 and cannula tip 16. The stop means is illustrated as a shoulder which may conveniently determine an insertion length L3 of the cannula which may be measured between stop means 30 and cannula tip 16. The function of the stop means is to limit the extent of insertion of the cannula 12 into a test tube closure as will be explained in greater detail. In the embodiment shown in FIG. 1, cannula 12 is shown as being provided with a plurality of serrations, teeth, or barbs 32 between the stop means 30 and the tip 16 for resisting any tendency to accidentally withdraw the cannula from a test tube closure. Thus the serrations and stop means cooperate to limit subsequent movement of dispenser 10 relative to a test tube closure after the apparatus has been attached to a test tube.

Cannula base 22 may be gripped or held during insertion of dispenser 10 into a test tube closure, thus facilitating the puncturing of the closure by cannula tip 16. Cannula stem 20, which includes a lower flared portion 34 provides structural support for the cannula, thus tending to prevent any accidental breakage of the cannula at its stem portion during insertion of the cannula into the test tube closure.

Figure 3:
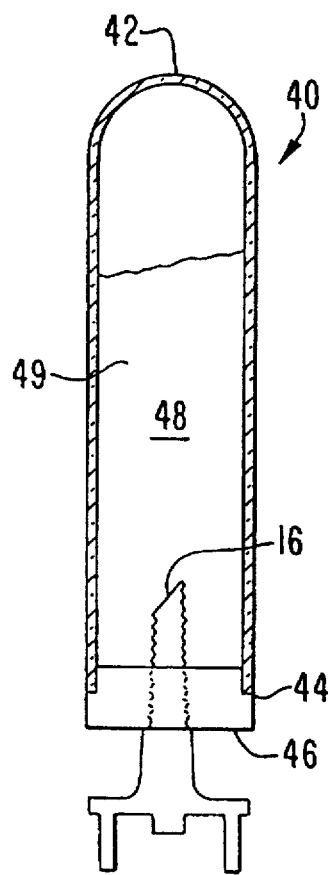
FIG. 3 is a sectional side elevational view of the apparatus of FIG. 1 after insertion through the closure of a sealed test tube but prior to the dispensing fluid.
Figure 4:
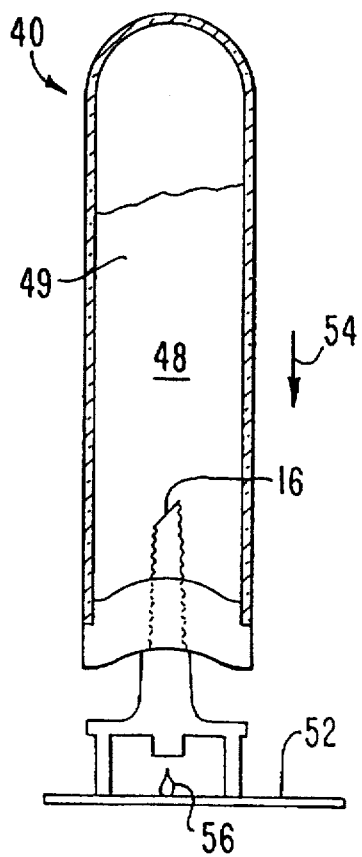
FIG. 4 is a sectional side elevational view of the apparatus of FIG. 1 diagrammatically illustrating pressurizing the chamber or interior of the test tube and dispensing fluid.

FIG. 3 illustrates the apparatus of the present invention after insertion through the closure of a test tube. Specifically, a conventional test tube 40 is illustrated in the inverted position with a closed end 42 and an open end 44. The test tube, which is of circular cross-section in plan view as is conventional, is closed with a conventional closure 46 which is of generally T shape in plan view, having an enlarged head, which forms a seal with the open end 44 of the test tube, and a depending leg which is inserted into the test tube. Closure 46 is well known as a reusable, resealable, repuncturable resilient stopper formed of rubber or the like which is force fit into the open end 44 of the test tube and frictionally retained in position. The interior 48 of the test tube is illustrated as having fluid 49 therein and may have an air space between the top of the fluid and the closed end 42 of the test tube. In FIG. 3 the dispenser 10 is illustrated as engaging the test tube closure or stopper. Specifically, the dispenser has been inserted through the stopper until the stop means 30 of the cannula 12 engages and abuts against the outer surface 50 of the flexible closure. The dispenser 10 is illustrated in FIG. 4 with the stabilizing means 28 resting on a target surface, such as a specimen plate 52.

The operation of the dispenser of the present invention will now be explained. In operation, the fluid 48 to be dispensed is first collected within the interior 48 of the test tube by conventional techniques. The dispenser 10 is then inserted through the test tube closure 46 and the test tube 40 (with dispenser 10 attached) is inverted into the position generally illustrated in FIG. 3. The dispenser 10 is then sighted with respect to the target surface, such as a specimen slide 52, by the user who views the position of the slide through the viewing spaces 35 or the transparent stabilizing means 28. The slide may be maneuvered through the legs 33 to obtain the desired location for the dispensing of the liquid 49. With the stabilizing means 28 positioned on or adjacent a specimen slide 52 or other surface, the test tube 40 may be moved toward the dispenser 10, in the direction of arrow 54, such that the stop means 30 causes flexing of the resilient stopper or closure 46. By moving the test tube 40 and dispenser 10 relative to each other to flex the closure 46 inwardly of the test tube 40 and thus reducing the volume within the test tube 40, the contents of the test tube 40 are pressurized.

Thus by manually gripping the test tube 40 and gently applying a downward force, the stop means cooperates with the closure to flex the closure inwardly of the test tube, thus reducing the volume (increasing the pressure) in response to which volume reduction a droplet 56 of fluid enters the fluid inlet 16, flows through the bore 14, exits through the fluid outlet 18, and is dispensed onto the specimen plate 52.

In an alternate form of the invention, the dispenser 10 may be held by the base 22, in one hand, and the test tube 40 moved toward the dispenser, such that the dispenser causes flexing of the stopper or closure and the resulting reduction of volume within the interior of the test tube. Thus the stabilizing means 28, while enhancing accuracy and efficiency in dispensing the fluid, is not required to accomplish the dispensing of fluid onto the target surface.

In each form of the invention, the flexing of the closure 46 into the interior or chamber 48 of the test tube, reduces the volume therein from a first volume to a second volume, thereby increasing the pressure within that chamber. Such a pressure increase ultimately results in a pumping or dispensing of a corresponding small volume 56 (such as a drop of fluid) from the test tube. This process can be repeated as many times as necessary after the first drop is dispensed by releasing tube 40 from a downward force in order to allow air to enter chamber 48 through bore 14 before resuming further dispensing of fluid therefrom by reapplying a downward force onto the test tube as described above.

In a preferred embodiment the dispenser 10 may be formed of impact styrene.

The foregoing is a complete description of the apparatus and method of the present invention. Various changes may be made without departing from the spirit and scope of the present invention. The invention, therefore, should be limited only by the scope of the claims which follow.

What is claimed is:

1. An apparatus for transferring fluid from a test tube having a closed end and an open end closed by a flexible closure, the test tube including a chamber, said chamber having a first volume and including fluid therein, the apparatus comprising:

means for puncturing the flexible closure for establishing a fluid flow path between the interior of the chamber and the exterior of the test tube, said puncturing means including means for flexing the flexible closure to decrease the first volume in the test tube so that fluid flows through the fluid flow path; and a stabilizing means including at least two depending legs with spaces disposed therebetween for stabilizing said puncturing means on a target surface when said flexible closure is being flexed and for flexing said flexible closure to decrease the first volume in the test tube, wherein said spaces permit a user to view the surface onto which the fluid is to be dispensed and to view the fluid as it is dispensed.

2. The apparatus of claim 1 wherein said stabilizing means includes three depending legs.

3. The apparatus of claim 1 wherein the stabilizing means is transparent.

4. The apparatus of claim 1 wherein the puncturing means has a serrated surface.

5. The apparatus of claim 1 wherein the dispensing means includes a shoulder for flexing said flexible closure.

6. A method of dispensing fluid from a fluid container, comprising:

providing a test tube having a closed end and an open end closed by a flexible closure, the test tube including a chamber, said chamber having a first volume and including fluid therein;

providing an apparatus having a dispenser means for puncturing the flexible closure for establishing a fluid flow path between the interior of the chamber and the exterior of the test tube, said dispenser means including means for flexing the flexible closure to decrease the first volume in the test tube so that fluid flows through the fluid flow path, and a stabilizing means for supporting said dispenser means on a support surface when said flexible closure is being flexed to decrease the first volume in the test tube, said stabilizing means having at least two depending legs with viewing spaces separating each leg;

providing a target surface onto which fluid is to be dispensed;

providing a support surface for the stabilizing means;

sighting the apparatus on the support surface through the viewing spaces; and depressing the tube towards the stabilizing means to decrease the volume therein and dispense the fluid within the tube through the flow path and onto the target surface.

7. The method of claim 6 wherein the stabilizing means has at least three depending legs.

8. The method of claim 7 wherein the stabilizing means is transparent and the target surface is sighted through stabilizing means.

* * * * *